(12) United States Patent
Ryan

(10) Patent No.: US 11,975,177 B2
(45) Date of Patent: May 7, 2024

(54) SUBCONJUNCTIVAL INJECTOR AND METHOD

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 166 days.

(21) Appl. No.: 16/180,998

(22) Filed: Nov. 5, 2018

(65) Prior Publication Data

US 2019/0070363 A1 Mar. 7, 2019

Related U.S. Application Data

(63) Continuation of application No. 14/777,288, filed as application No. PCT/US2014/026749 on Mar. 13, 2014, now abandoned.
(Continued)

(51) Int. Cl.
*A61M 5/30* (2006.01)
*A61F 9/00* (2006.01)
(Continued)

(52) U.S. Cl.
CPC .............. *A61M 5/30* (2013.01); *A61F 9/0008* (2013.01); *A61M 5/46* (2013.01); *A61F 9/0026* (2013.01); *A61M 2037/0023* (2013.01)

(58) Field of Classification Search
CPC .... A61M 2005/2006; A61M 2005/208; A61M 2005/206; A61M 5/30; A61M 5/425; A61M 2037/0023; A61M 37/0015; A61M 2037/003; A61M 2037/0038; A61M 5/46; A61M 5/148; A61M 5/1483; A61M 5/1486; A61M 5/152; A61M 5/2425;
(Continued)

(56) References Cited

U.S. PATENT DOCUMENTS

| 4,543,096 A | 9/1985 | Keene |
| 7,678,078 B1 | 3/2010 | Peyman et al. |

(Continued)

FOREIGN PATENT DOCUMENTS

| WO | WO-2012006677 A1 * | 1/2012 | ......... A61B 5/14503 |
| WO | WO-2012059517 A1 | 5/2012 | |

(Continued)

OTHER PUBLICATIONS

U.S. Appl. No. 14/777,288, Advisory Action dated Nov. 7, 2017, 4 pgs.
(Continued)

*Primary Examiner* — Deanna K Hall
*Assistant Examiner* — Alexandra LaLonde
(74) *Attorney, Agent, or Firm* — Schwegman Lundberg & Woessner, P.A.

(57) ABSTRACT

An injection device and method are shown. Devices and methods include a forceps and a needle advancement mechanism to clamp a portion of tissue and control a depth of penetration of the needle between gripping ends of the forceps. An injection device and method are shown where selected components of the injection device such as a syringe and forceps are disposable, while the remaining portions of the injection device are reusable. Devices and methods are shown that utilize micro-needles to control a depth of penetration.

3 Claims, 6 Drawing Sheets

Related U.S. Application Data

(60) Provisional application No. 61/935,239, filed on Feb. 3, 2014, provisional application No. 61/787,684, filed on Mar. 15, 2013.

(51) Int. Cl.
*A61M 5/46* (2006.01)
*A61M 37/00* (2006.01)

(58) Field of Classification Search
CPC ............ A61M 5/14224; A61M 5/1458; A61M 5/14593; A61F 9/0008; A61F 9/0017; A61F 9/0026
See application file for complete search history.

(56) References Cited

U.S. PATENT DOCUMENTS

| | | |
|---|---|---|
| 2006/0002900 A1 | 1/2006 | Binder et al. |
| 2006/0111738 A1 | 5/2006 | Wenchell |
| 2008/0312669 A1 | 12/2008 | Vries et al. |
| 2009/0030414 A1 | 1/2009 | Bayat |
| 2009/0076443 A1 | 3/2009 | Slate et al. |
| 2010/0100054 A1* | 4/2010 | Cormier ............... A61F 9/0017 604/239 |
| 2010/0241102 A1 | 9/2010 | Ma |
| 2012/0226260 A1* | 9/2012 | Prausnitz ............... A61F 9/0017 604/506 |
| 2016/0038680 A1 | 2/2016 | Ryan |

FOREIGN PATENT DOCUMENTS

| | | |
|---|---|---|
| WO | WO-2012112699 A2 | 8/2012 |
| WO | WO-2014151970 A2 | 9/2014 |
| WO | WO-2014151970 A3 | 9/2014 |

OTHER PUBLICATIONS

U.S. Appl. No. 14/777,288, Advisory Action dated Dec. 5, 2017, 3 pgs.
U.S. Appl. No. 14/777,288, Final Office Action dated May 4, 2018, 17 pgs.
U.S. Appl. No. 14/777,288, Final Office Action dated Aug. 16, 2017, 15 pgs.
U.S. Appl. No. 14/777,288, Non Final Office Action dated Jan. 12, 2018, 15 pgs.
U.S. Appl. No. 14/777,288, Non Final Office Action dated Apr. 27, 2017, 17 pgs.
U.S. Appl. No. 14/777,288, Preliminary Amendment filed Sep. 15, 2015, 3 pgs.
U.S. Appl. No. 14/777,288, Response filed Apr. 12, 2018 to Non Final Office Action dated Jan. 12, 2018, 7 pgs.
U.S. Appl. No. 14/777,288, Response filed Apr. 17. 2017—to Restriction Requirement dated Feb. 15, 2017, 5 pgs.
U.S. Appl. No. 14/777,288, Response filed Oct. 16, 2017 to Final Office Action dated Aug. 16, 2017, 7 pgs.
U.S. Appl. No. 14/777,288, Response filed Nov. 16, 2017 to Advisory Action dated Nov. 7, 2017, 7 pgs.
U.S. Appl. No. 14/777,288, Response filed Jul. 27, 2017 to Non Final Office Action dated Apr. 27, 2017, 8 pgs.
U.S. Appl. No. 14/777,288, Restriction Requirement dated Feb. 15, 2017, 7 pgs.
International Application Serial No. PCT/US2014/026749, International Search Report dated Oct. 17, 2014, 4 pgs.
International Application Serial No. PCT/US2014/026749, Invitation to Pay Additional Fees dated Aug. 5, 2014, 2 pgs.
International Application Serial No. PCT/US2014/026749, Written Opinion dated Oct. 17, 2014, 7 pgs.

\* cited by examiner

SUBCONJUNCTIVAL INJECTOR AND METHOD

CLAIM OF PRIORITY

This application is a continuation of and claims the benefit of priority under 35 U.S.C. § 120 to U.S. patent application Ser. No. 14/777,288, filed on Sep. 15, 2015, which is a U.S. National Stage Filing under 35 U.S.C, 371 from International Application No. PCT/US2014/026749, filed on Mar. 13, 2014, and published as WO 2014/151970 A2 on Sep. 25, 2014, which claims the benefit of priority to U.S. Provisional Patent Application No. 61/787,684, filed Mar. 15, 2013, and to U.S. Provisional Patent Application No. 61/935,239, filed Feb. 3, 2014, each of which is incorporated herein by reference in its entirety.

TECHNICAL FIELD

This invention relates to ophthalmological injections.

BACKGROUND

Ophthalmological injections such as subconjunctival injections are necessary in a number of procedures. It is desirable to increase the repeatability of injection procedures, and to increase the ease of performing injections, and to increase the safety of such injections.

DETAILED DESCRIPTION

Figure 1:
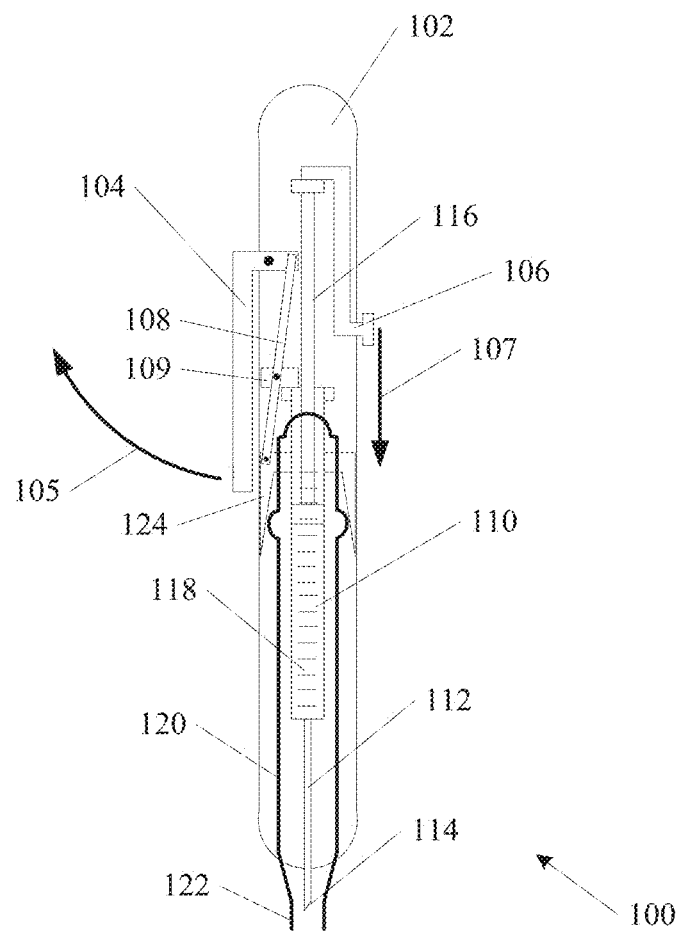
FIG. 1 shows an injection device according to an embodiment of the invention.

In the following detailed description, reference is made to the accompanying drawings which form a part hereof, and in which is shown, by way of illustration, specific embodiments in which the invention may he practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an injection device 100 according to an embodiment of the invention. The injection device 100 of FIG. 1 includes a body 102 housing a number of additional components. A drug reservoir 118 is shown within the body 102, and a needle 112 connected to the drug reservoir 118. A forceps 120 are also shown within the body 102. A first actuator 104 is operatively coupled to the needle 112. When actuated, the first actuator 104 advances a tip 114 of the needle 112 forward between gripping ends 122 of the forceps 120. A range of travel of the needle 112 is limited by the first actuator 104 and the gripping ends 122 of the forceps 120. In this way, when in use, delivering a drug such as an anesthetic to an eye, the tip 114 of the needle 112 is assured to consistently penetrate the conjunctiva to an effective depth, without penetrating too deep. Although an anesthetic injection is used as an example, injection devices as described in the present disclosure may be used to administer any number of different drugs.

Figure 2:
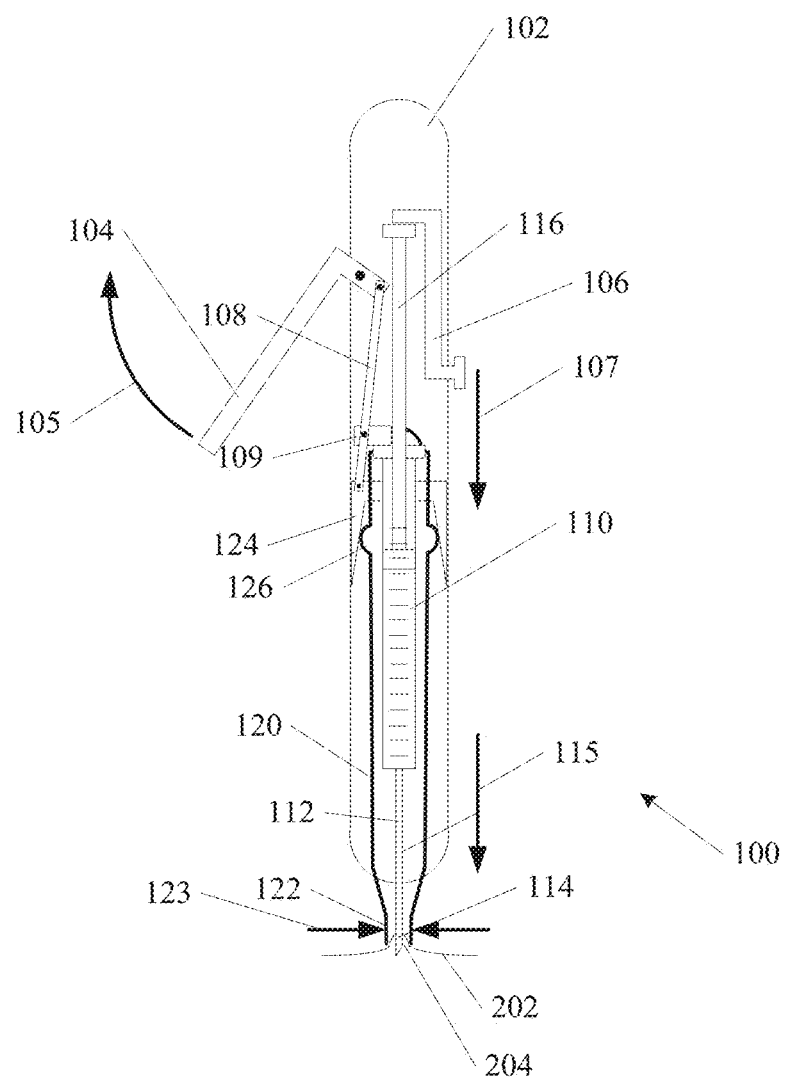
FIG. 2 shows the injection device of claim 1 in operation according to an embodiment of the invention.

In the example of FIG. 1, the first actuator 104 is moved along arc 105. The motion of the first actuator 104 is translated through a linkage 108, which is coupled to a wedge 124. As the wedge 124 is forced downward, the gripping ends 122 of the forceps 120 are closed. FIG. 2 shows the first actuator 104 in operation. The wedge 124 pushes against protrusions 126 on the forceps 120 and causes the gripping ends 122 to close as indicated by arrows 123. A portion 204 of tissue 202, such as a portion of a conjunctiva, is bunched up between the gripping ends 122. The tip 114 of the needle 112 then penetrates into the portion 204 of tissue 202.

In the example of FIGS. 1 and 2, a second linkage 109 is coupled to the first linkage 108 such that in addition to actuating a clamping of the gripping ends 122, the needle 112 is urged in direction 115. In one example, the linkages 108, 109 are timed such that the gripping ends 122 are clamped first, and the needle 112 is urged in direction 115 after the gripping ends 122 are clamped. In one example, the gripping ends 122 and the needle 112 are actuated at the same time.

In the example shown, the first actuator 104 operates as a single actuator to move both the gripping ends 122 and the needle 112. In other examples, these operations may be performed by separate actuators.

Although examples of linkages and actuator configurations are shown, the invention is not limited to any one actuation method or type of actuating lever, button, etc. Other linkages and actuators such as pneumatic, hydraulic, electric motor driven operation, solenoid, etc. are within the scope of the invention. Further, other actuators apart from levers may be used without departing from the scope of the invention. For example buttons, knobs or other effective actuators may be used to facilitate gripping of the forceps 120 and controlled motion of the needle 112. In one example one or more of the actuators is electrically powered, and the injection device 100 includes one or more batteries to power the one or more actuators.

FIG. 1 further shows a second actuator 106. In one example, after using the first actuator 104 to grip a portion of tissue, such as a conjunctiva, and advancing the needle 112 into the gripped portion of tissue, the second actuator 106 is moved long direction 107, and is used to expel an amount of a drug into the tissue penetrated by the needle 112. Configurations such as the example shown provide ease of use, in that the tissue is gripped and the needle consistently penetrates to the desired depth using a single control, and the drug is easily delivered when desired using the second control.

In the configuration shown, the drug reservoir 118 is part of a standard hypodermic syringe 110. The syringe 110 includes a plunger 116 that interacts with the second actuator 106. In one example the syringe 110 is disposable, while the remaining components of the injection device 100 are reusable. In one example the forceps 120 are disposable, while the remaining components of the injection device 100 are reusable. In one example, both the syringe 110 and the forceps 120 are disposable, while the remaining components of the injection device 100 are reusable.

Figure 3:
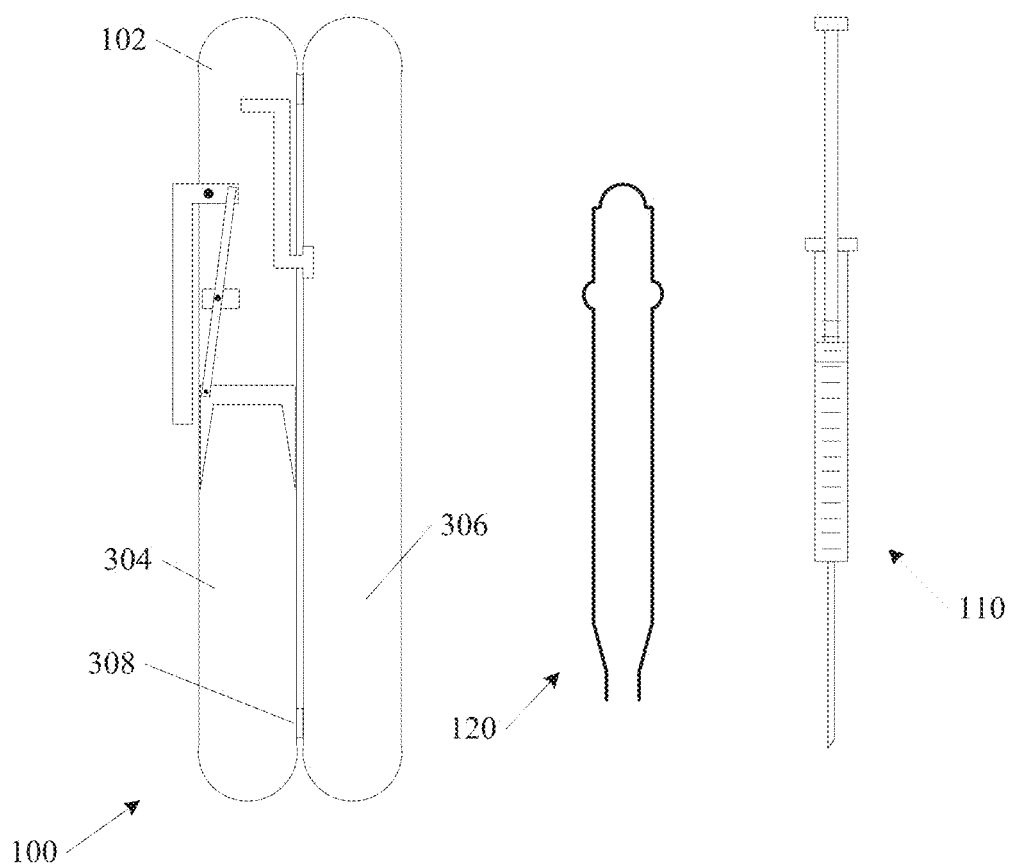
FIG. 3 shows individual components of an injection device according to an embodiment of the invention.

FIG. 3 illustrates one example where the syringe 110 and forceps 120 may be removed from the body 102 of the injection device 100. In the example shown, the body 102, includes a first portion 304 and a second portion 306 that are hinged 308. In the example shown, the portions 304, 306 are approximately halves of the body 102, although the invention is not so limited. In one example, one portion, such as portion 306 is formed of a substantially clear material, such as clear plastic. When in use, such a configuration allows a user to see if the syringe 110 is full with an appropriate dose of the desired drug.

An advantage of an example injection device 100 where selected components are removable and disposable includes reduced cost of components, and better ability to sterilize components that will be in contact with a patient. Because a majority of the injection device 100 is reusable, and the cost of elements such as the syringe 110 and forceps 120 that are disposed of are at a minimum, the cost of an injection procedure is reduced. In one example, the forceps are formed from a clear plastic material. Such a configuration reduces cost, and allows the user to better see the tissue where an injection is taking place.

Figure 4:
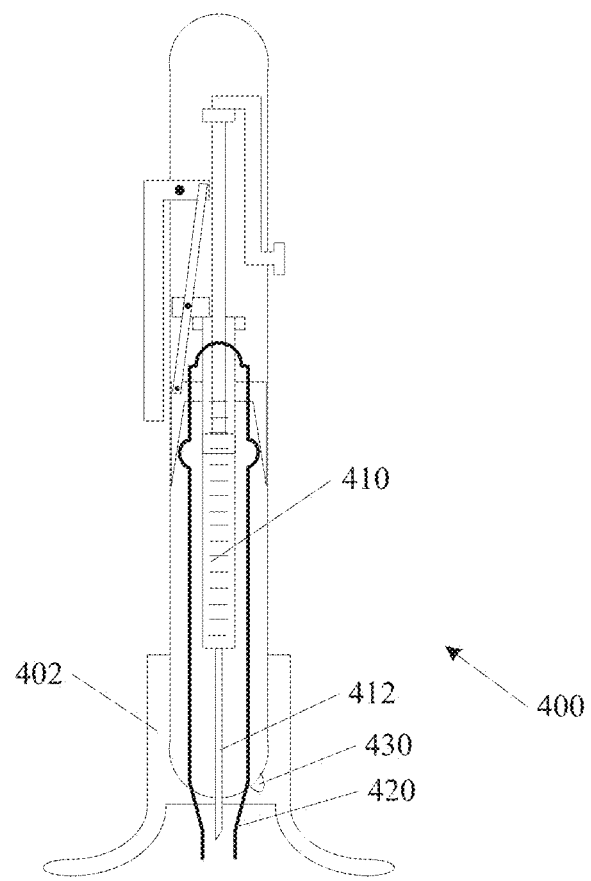
FIG. 4 shows another injection device according to an embodiment of the invention.

FIG. 4 shows another example injection device 400 according to an embodiment of the invention. In one example, the injection device 400 operates similar to examples described above. A forceps 420 are included, along with a syringe 410. A needle 412 may be advanced using an actuator along with clamping of tissue using the forceps 420. FIG. 4 further illustrates a speculum 402 that may be used to hold a patient's eyelids apart during an injection procedure. In one example, the speculum 402 is disposable, while the remaining components of the injection device 400 are reusable. As in examples above, in addition to the speculum 402 being reusable, in one example the syringe 410 is disposable, while the remaining components of the injection device 400 are reusable. In one example the forceps 420 are disposable, while the remaining components of the injection device 400 are reusable.

In one example, a light 430 is included at a distal end of the injection device 400. Examples of the light 430 include, but are not limited to an LED light.

Figure 5:
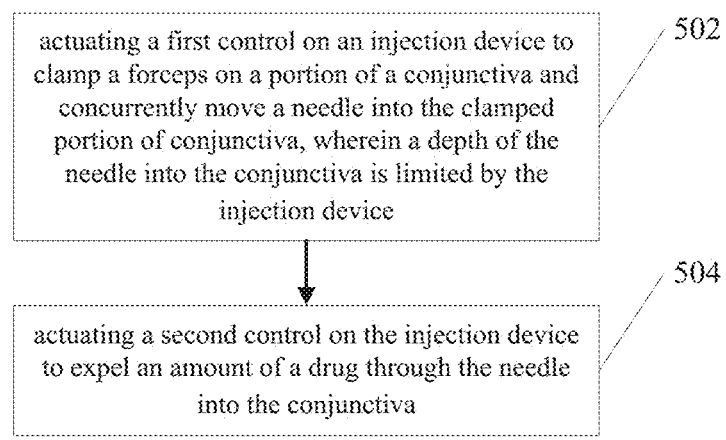
FIG. 5 shows a method of using an injection device according to an embodiment of the invention.

FIG. 5 illustrates an example method of use according to an embodiment of the invention. In operation 502, a first control on an injection device is actuated to clamp a forceps on a portion of a conjunctiva and concurrently move a needle into the clamped portion of conjunctiva, wherein a depth of the needle into the conjunctiva is limited by the injection device. In operation 504, a second control on the injection device is actuated to expel an amount of a drug through the needle into the conjunctiva.

Figure 6:
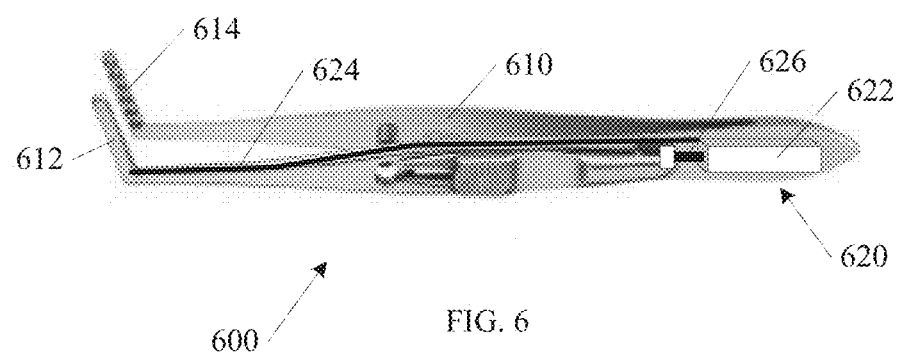
FIG. 6 shows another injection device according to an embodiment of the invention.

FIG. 6 shows another example injection device 600 according to an embodiment of the invention. The injection device 600 includes a forceps handle 610, having a pair of paddles 612 for grasping a conjunctiva of a patient's eye. At least one paddle 612 includes a number of micro-needles 614. In one example, the micro-needles 614 are dimensioned to break a surface of the conjunctiva, but are not long enough to penetrate into any structure beneath. In one example, the micro-needles 614 will penetrate the conjunctiva, but will not penetrate the sclera. In one example, the micro-needles 614 are less than approximately 0.30 mm long. In one example, the micro-needles 614 are less than approximately 0.50 mm long.

In one example, the injection device 600 includes a drug delivery system 620 that is coupled to the micro-needles 614. The example of FIG. 6 shows a reservoir 622 coupled to a tube 624 and an actuator 626. In one example, the actuator 626 includes a piston or plunger that forces a drug from the reservoir 622 through the tube 624 into the micro-needles 614. In one example, the micro-needles 614 are located on only one paddle 612. In one example, both paddles 612 may include micro-needles 614. In one example, the drug that is delivered includes an anesthetic.

Figure 7:
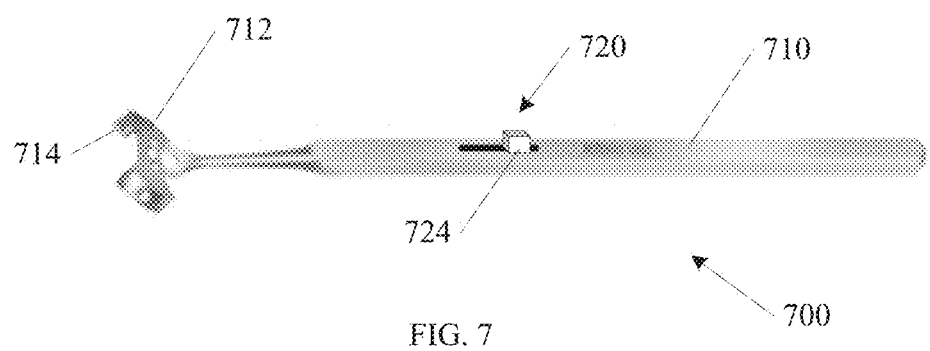
FIG. 7 shows another injection device according to an embodiment of the invention.

FIG. 7 shows another example injection device 700 according to an embodiment of the invention. A handle 710 is coupled to a plate 712 that is shaped to be places against the conjunctiva of a patient's eye. A number of Micro-needles 714 are located on a face of the plate 712. Similar to the example injection device 600 of FIG. 6, the micro-needles 714 are dimensioned to break a surface of the conjunctiva, hut are not long enough to penetrate into any structure beneath. In one example, the micro-needles 714 will penetrate the conjunctiva, but will not penetrate the sclera. In one example, the micro-needles 714 are less than approximately 0.30 mm long. In one example, the micro-needles 714 are less than approximately 0.50 mm long.

In one example, the injection device 700 includes a drug delivery system 720 that is coupled to the micro-needles 714. In one example a reservoir (not shown) is located within the handle 710 and an actuator 724 is located on the handle 710. In one example, the actuator 724 is coupled to a piston or plunger that forces a drug from the reservoir into the micro-needles 714. As in the injection device 600 of FIG. 6, in one example, the drug that is delivered includes an anesthetic.

While a number of advantages of embodiments described herein are listed above, the list is not exhaustive. Other advantages of embodiments described above will be apparent to one of ordinary skill in the art, having read the present disclosure. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:
1. An injection device, comprising:
a forceps, including a pair of opposing handles that join together at a proximal end;
a pair of paddles coupled respectively to the ends of the pair of opposing handles, wherein a surface of each of the paddles in the pair of paddles contains a plurality of micro-needles, wherein the plurality of micro-needles are dimensioned to penetrate a surface of a conjunctiva, but are not long enough to penetrate a sclera;
a drug delivery system integrated into the opposing handles of the forceps, including:
a reservoir located at the proximal end, and the plurality of micro-needles located at a distal end of the pair of opposing handles, the reservoir coupled to the plurality of micro-needles by tubing located between the reser- voir and the plurality of micro-needles, the reservoir including an amount of anesthetic; and an actuator to deliver the anesthetic from the reservoir through to the plurality of micro-needles.

2. The injection device of claim 1, wherein the plurality of micro-needles are less than approximately 0.50 mm long.

3. The injection device of claim 1, wherein the plurality of micro-needles are less than approximately 0.30 mm long.

\* \* \* \* \*